(12) United States Patent
Zoeller et al.

(10) Patent No.: US 6,537,944 B1
(45) Date of Patent: Mar. 25, 2003

(54) TUNGSTEN PROMOTED CATALYST FOR CARBONYLATION OF LOWER ALKYL ALCOHOLS

(75) Inventors: Joseph Robert Zoeller, Kingsport, TN (US); Andy Hugh Singleton, Kingsport, TN (US); Gerald Charles Tustin, Kingsport, TN (US); Donald Lee Carver, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/885,190

(22) Filed: Jun. 20, 2001

(51) Int. Cl.[7] .......................... B01J 21/18; B01J 27/06; B01J 27/132; B01J 27/13; B01J 23/42
(52) U.S. Cl. .................. 502/180; 502/339; 502/181; 502/182; 502/185; 502/228; 502/230; 502/313
(58) Field of Search .................. 502/180–182, 502/185, 228, 230, 313, 339; 560/207, 232, 97, 99; 562/519; 554/128, 131

(56) References Cited

U.S. PATENT DOCUMENTS

| | | |
|---|---|---|
| 3,689,533 A | 9/1972 | Schultz |
| 3,717,670 A | 2/1973 | Schultz |
| 3,772,380 A | 11/1973 | Paulik et al. |
| 4,417,077 A | 11/1983 | Drago et al. |
| 4,612,387 A | 9/1986 | Feitler |
| 4,625,049 A | 11/1986 | Current |
| 4,776,987 A | 10/1988 | Luft et al. |
| 4,845,163 A | 7/1989 | Panster et al. |
| 4,918,218 A | 4/1990 | Mueller et al. |
| 5,144,068 A | 9/1992 | Smith et al. |
| 5,185,462 A | 2/1993 | Evans et al. |
| 5,218,140 A | 6/1993 | Wegman |
| 5,258,549 A | 11/1993 | Pimblett |
| 5,414,161 A | 5/1995 | Uhm et al. |
| 5,488,143 A | 1/1996 | Uhm et al. |
| 5,510,524 A | 4/1996 | Garland et al. |
| 5,874,652 A | 2/1999 | Pitchai et al. |
| 5,900,505 A | 5/1999 | Tustin et al. |
| 6,160,163 A | 12/2000 | Zoeller et al. |
| 6,235,673 B1 | 5/2001 | Zoeller et al. |

FOREIGN PATENT DOCUMENTS

| | | |
|---|---|---|
| EP | 0 120 631 A1 | 10/1984 |
| EP | 0 130 058 A1 | 1/1985 |
| EP | 0 343 475 A2 | 11/1989 |
| EP | 0 461 802 A2 | 12/1991 |
| EP | 0 596 632 A1 | 5/1994 |
| EP | 0 749 948 A1 | 12/1996 |
| EP | 0 752 406 A1 | 1/1997 |
| EP | 0 759 419 A1 | 2/1997 |
| WO | WO 98/33590 | 8/1998 |
| WO | WO 98/33759 | 8/1998 |
| WO | WO 00/48979 | 8/2000 |

OTHER PUBLICATIONS

P. Gelin, C. Naccache, and Y. Taarit, "Coordination Chemistry of Rhodium and Iridium in Constrained Zeolite Cavities: Methanol Carbonylation", *Pure & Appl. Chem.*, vol. 60, No. 8, (1988) p. 1315–1320, Great Britain, month not avail.

H. Yagita, K. Omata, H. Tominaga and K. Fujimoto, "Vapor–phase Carbonylation of Methanol Over Lead on Active Carbon Catalyst", *Catalysis Letters*, 2 (1989) p. 145–148, Germany, month not avail.

H. Yagita and K. Fujimoto, "Redox Cycle of Metal–on–Active Carbon Catalyst in the Vapor Phase Carbonylation of Methanol", *Journal of Molecular Catalyst*, 69 (1991) p. 191–197, Netherlands, month not avail.

K. Fujimoto, S. Bischoff, K. Omata and H. Yagita, "Hydrogen Effects on Nickel–Catalyzed Vapor–Phase Methanol Carbonylation", *Journal of Catalysis*, 133 (1992) p. 370–382, month not avail.

M. J. Howard, M. D. Jones, M. S. Roberts and S. A. Taylor, "$C_1$ to Acetyls: Catalysis and Process", *Catalysis Today*, 18 (1993) p. 325–354, Amsterdam, month not avail.

T. Liu and S. Chiu, "Promoting Effect of Tin on Ni/C Catalyst for Methanol Carbonylation", *Ind. Eng. Chem. Res.*, 33 (1994) p. 488–492, USA, month not avail.

A. Krzywicki and M. Marczewski, "Formation and Evolution of the Active Site for Methanol Carbonylation on Oxide Catalysts Containing $RhCl_3$", *Journal of Molecular Catalysis*, 6 (1979) p. 431–440, Netherlands, month not avail.

K. Fujimoto, H. Mazaki, K. Omata and H. Tominaga, "Promotion Effect of Hydrogen on Vapor Phase Carbonylation of Methanol Over Nickel on Active Carbon Catalyst", *Chemistry Letters*, (1987) p. 895–898, Japan, month not avail.

H. E. Maneck, D. Gutschick, I. Burkardt, B. Luecke, H. Miessner, and U. Wolf, "Heterogeneous Carbonylation of Methanol on Rhodium Introduced Into Faujasite–Type Zeolites", *Catalysis Today*, 3 (1988) p. 421–429, Netherlands, month not avail.

K. M. Webber, B. C. Gates and W. Drenth, "Design and Synthesis of a Solid Bifunctional Polymer Catalyst for Methanol Carbonylation," *Journal of Molecular Catalysis*, 3, (1977/78), p. 1–9, Netherlands, month not avail.

*Primary Examiner*—Mark L. Bell
*Assistant Examiner*—Patricia L. Hailey
(74) *Attorney, Agent, or Firm*—Jonathan Wood; Bernard J. Graves, Jr.

(57) ABSTRACT

A solid carbonylation catalyst useful for producing esters and carboxylic acids from reactants including lower alkyl alcohols and lower alkyl alcohol producing compositions in a vapor phase carbonylation process wherein the catalyst includes a catalytically effective amount of a Group VIII metal selected from platinum or palladium, and tungsten which are associated with a solid catalyst support material.

21 Claims, No Drawings

TUNGSTEN PROMOTED CATALYST FOR CARBONYLATION OF LOWER ALKYL ALCOHOLS

BACKGROUND OF THE INVENTION

The present invention relates to a solid catalyst and particularly to a solid catalyst useful for producing esters and carboxylic acids in the vapor-phase carbonylation of lower alkyl alcohols, lower alkyl alcohol producing compositions, and mixtures thereof. More particularly, the present invention relates to a solid catalyst which includes an effective amount of a Group VIII metal selected from platinum or palladium, and tungsten. The metals are associated with a solid carrier material. The carbonylation catalyst is particularly useful for the production of acetic acid, methyl acetate and mixtures thereof from methanol, methanol generating compounds and mixtures thereof.

Lower carboxylic acids and esters such as acetic acid and methyl acetate have been known as industrial chemicals for many years. Acetic acid is used in the manufacture of a variety of intermediary and end-products. For example, an important derivative is vinyl acetate which can be used as monomer or co-monomer for a variety of polymers. Acetic acid itself is used as a solvent in the production of terephthalic acid, which is widely used in the container industry, and particularly in the formation of PET beverage containers.

There has been considerable research activity in the use of metal catalysts for the carbonylation of lower alkyl alcohols, such as methanol, and ethers to their corresponding carboxylic acids and esters.

Carbonylation of methanol is a well known reaction and is typically carried out in the liquid phase with a catalyst. A thorough review of these commercial processes and other approaches to accomplishing the formation of acetyl from a single carbon source is described by Howard et al. in *Catalysis Today*, 18 (1993) 325–354. Generally, the liquid phase carbonylation reaction for the preparation of acetic acid using methanol is performed using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst. For example, U.S. Pat. No. 5,510,524 to Garland et. al. describes a liquid phase carbonylation process for the production of carboxylic acid by carbonylation of an alkyl alcohol and/or reactive derivative by contacting the alcohol with carbon monoxide in a liquid reaction composition which includes an iridium catalyst or rhodium catalyst, an alkyl halide, water and a rhenium promoter.

A disadvantage of a homogeneous phase carbonylation process is that additional steps are necessary for separating the products from the catalyst solutions, and there are always handling losses of the catalyst. Losses of the metal in the catalyst can be attributed to several factors, such as the plating-out of the active metal onto piping and process equipment thereby rendering the metal inactive for carbonylation purposes and losses due to incomplete separation of the catalyst from the products. These losses of the metal component are costly because the metals themselves are very expensive.

U.S. Pat. No. 5,144,068 describes the inclusion of lithium in the catalyst system which allows the use of less water in the Rh-I homogeneous process. Iridium also is an active catalyst for methanol carbonylation reactions but normally provides reaction rates lower than those offered by rhodium catalysts when used under otherwise similar conditions.

European Patent Application EP 0 752 406 A1 teaches that ruthenium, osmium, rhenium, zinc, cadmium, mercury, gallium, indium, or tungsten improve the rate and stability of the liquid phase Ir-I catalyst system. Generally, the homogeneous carbonylation processes presently being used to prepare acetic acid provide relatively high production rates and selectivity. However, heterogeneous catalysts offer the potential advantages of easier product separation, lower cost materials of construction, facile recycle, and even higher rates.

Schultz, in U.S. Pat. No. 3,689,533, discloses using a supported rhodium heterogeneous catalyst for the carbonylation of alcohols to form carboxylic acids in a vapor phase reaction. Schultz further discloses the presence of a halide promoter.

Schultz in U.S. Pat. No. 3,717,670 describes a similar supported rhodium catalyst in combination with promoters selected from Groups IB, IIIB, IVB, VB, VIB, VIII, lanthanide and actinide elements of the Periodic Table.

Uhm, in U.S. Pat. No. 5,488,143, describes the use of alkali, alkaline earth or transition metals as promoters for supported rhodium for the halide-promoted, vapor phase methanol carbonylation reaction. Pimblett, in U.S. Pat. No. 5,258,549, teaches that the combination of rhodium and nickel on a carbon support is more active than either metal by itself.

In addition to the use of iridium as a homogeneous alcohol carbonylation catalyst, Paulik et al., in U.S. Pat. No. 3,772, 380, describe the use of iridium on an inert support as a catalyst in the vapor phase, halogen-promoted, heterogeneous alcohol carbonylation process.

European Patent Applications EP 0 120 631 A1 and EP 0 461 802 A2 describe the use of special carbons as supports for single transition metal component carbonylation catalysts.

European Patent Application EP 0 759 419 A1 pertains to a process for the carbonylation of an alcohol and/or a reactive derivative thereof.

EP 0 759 419 A1 discloses a carbonylation process comprising a first carbonylation reactor wherein an alcohol is carbonylated in the liquid phase in the presence of a homogeneous catalyst system and the off gas from this first reactor is then mixed with additional alcohol and fed to a second reactor containing a supported catalyst. The homogeneous catalyst system utilized in the first reactor comprises a halogen component and a Group VIII metal selected from rhodium and iridium. When the Group VIII metal is iridium, the homogeneous catalyst system also may contain an optional co-promoter selected from the group consisting of ruthenium, osmium, rhenium, cadmium, mercury, zinc, indium and gallium. The supported catalyst employed in the second reactor comprises a Group VIII metal selected from the group consisting of iridium, rhodium, and nickel, and an optional metal promoter on a carbon support. The optional metal promoter may be iron, nickel, lithium and cobalt. The conditions within the second carbonylation reactor zone are such that mixed vapor and liquid phases are present in the second reactor. The presence of a liquid phase component in the second reactor inevitably leads to leaching of the active metals from the supported catalyst which, in turn, results in a substantial decrease in the activity of the catalyst and costly replacement of the active catalyst component.

The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today*, 3 (1988), 421–429. Gelin et al., in *Pure & Appl. Chem.*, Vol 60, No. 8, (1988) 1315–1320, provide examples of the use of rhodium or iridium contained in zeolite as catalysts for the vapor phase carbonylation of methanol in the presence of halide promoter. Krzywicki et al., in *Journal of Molecular Catalysis*, 6 (1979) 431–440, describe the use of silica, alumina, silica-alumina and titanium dioxide as supports for rhodium in the halide-promoted vapor phase carbonylation of methanol, but these supports are generally not as efficient as carbon. Luft et al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides.

Evans et al., in U.S. Pat. No. 5,185,462, describe heterogeneous catalysts for halide-promoted vapor phase methanol carbonylation based on noble metals attached to nitrogen or phosphorus ligands attached to an oxide support.

Panster et al., in U.S. Pat. No. 4,845,163, describe the use of rhodium-containing organopolysiloxane-ammonium compounds as heterogeneous catalysts for the halide-promoted liquid phase carbonylation of alcohols.

Drago et al., in U.S. Pat. No. 4,417,077, describe the use of anion exchange resins bonded to anionic forms of a single transition metal as catalysts for a number of carbonylation reactions including the halide-promoted carbonylation of methanol, Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component. Typically, these catalysts are unstable at elevated temperatures making them poorly suited to vapor phase processes.

Nickel on activated carbon has been studied as a heterogeneous catalyst for the halide-promoted vapor phase carbonylation of methanol, and increased rates are observed when hydrogen is added to the feed mixture. Relevant references to the nickel-on-carbon catalyst systems are provided by Fujimoto et al. In *Chemistry Letters* (1987) 895–898 and in *Journal of Catalysis*, 133 (1992) 370–382 and in the references contained therein. Liu et al., in *Ind. Eng. Chem. Res.*, 33 (1994) 488–492, report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general, the rates of reaction provided by nickel-based catalysts are lower than those provided by the analogous rhodium-based catalysts when operated under similar conditions.

Other single metals supported on carbon have been reported by Fujimoto et al. in *Catalysis Letters*, 2 (1989) 145–148 to have limited activity in the halide-promoted vapor phase carbonylation of methanol. The most active of these metals is Sn. Following Sn in order of decreasing activity are Pb, Mn, Mo, Cu, Cd, Cr, Re, V, Se, W, Ge and Ga. None of these other single metal catalysts are nearly as active as those based on Rh, Ir, Ni or the catalyst of the present invention.

A number of solid materials have been reported to catalyze the carbonylation of methanol without the addition of the halide promoter. Gates et al., in *Journal of Molecular Catalysis*, 3 (1977/78) 1–9, describe a catalyst containing rhodium attached to polymer bound polychlorinated thiophenol for the liquid phase carbonylation of methanol. Current, in European Patent Application EP 0 130 058 A1, describes the use of sulfided nickel containing optional molybdenum as a heterogeneous catalyst for the conversion of ethers, hydrogen and carbon monoxide into homologous esters and alcohols.

Smith et al., in European Patent Application EP 0 596 632 A1, describe the use of mordenite zeolite containing Cu, Ni, Ir, Rh, or Co as catalysts for the halide-free carbonylation of alcohols. Feitler, in U.S. Pat. No. 4,612,387, describes the use of certain zeolites containing no transition metals as catalysts for the halide-free carbonylation of alcohols and other compounds in the vapor phase.

U.S. Pat. No. 5,218,140 to Wegman describes a vapor phase process for converting alcohols and ethers to carboxylic acids and esters by the carbonylation of alcohols and ethers with carbon monoxide in the presence of a metal ion exchanged heteropoly acid supported on an inert support. The catalyst used in the reaction includes a polyoxometalate anion in which the metal is at least one of a Group V(a) and VI(a) is complexed with at least one Group VIII cation such as Fe, Ru, Os, Co, Rh, Ir, Ni, Pd or Pt as catalysts for the halide-free carbonylation of alcohols and other compounds in the vapor phase. The general formula of a preferred form of the heteropoly acid used in the practice of the process is $M[Q_{12}PO_{40}]$ where M is a Group VIII metal or a combination of Group VIII metals, Q is one or more of tungsten, molybdenum, vanadium, niobium, chromium, and tantalum, P is phosphorous and O is oxygen.

U.S. Pat. No. 5,900,505 to Tustin et al. describes a vapor-phase carbonylation catalyst having iridium and at least one second metal selected from ruthenium, molybdenum, tungsten, palladium, platinum and rhenium deposited on a catalyst support material.

U.S. Pat. No. 5,414,161 to Uhm et al. describes a process for the production of ethanol using gas phase carbonylation of methanol. The catalyst used in the process includes a rhodium compound and a second metallic component selected from an alkali metal, alkaline earth metal or a transition metal deposited on a support material.

Accordingly, there is a need for a catalyst which can be used in a vapor phase carbonylation process for the production of carboxylic acids and their esters and in which the catalyst is maintained in the solid phase.

SUMMARY OF THE INVENTION

Briefly, the present invention is for a solid catalyst useful for the vapor-phase carbonylation of lower alkyl alcohols, lower alkyl alcohol generating compounds, such as ether and ester derivatives of the alcohols, and mixtures thereof for producing esters and carboxylic acids. The catalyst includes a Group VIII metal selected from platinum or palladium and/or their respective metal containing compound, and tungsten and/or tungsten containing compound. The metals are associated with a solid carrier material which, desirably, is inert to the carbonylation reaction. In a preferred embodiment, the catalyst further includes a vaporous component comprising a halide promoter. As used herein the term "associated with" includes any manner that permits the platinum or palladium metal and/or a compound containing the metal, such as a salt thereof, and the tungsten metal and/or a tungsten containing compound to reside on or in the solid support. Non-limiting examples in which the metals may be associated with the solid support include impregnating, immersing, spraying, and coating the support sequentially with a solution containing the Group VIII metal and then with a tungsten containing solution. Alternatively, the Group VIII and tungsten metals may be associated with the solid support by impregnating, immersing, spraying, or coating the support with a solution containing a mixture of the Group VIII metal and tungsten.

It is an object of the present invention to provide a catalyst useful in a vapor-phase carbonylation process. It is another object of the invention to provide a vapor-phase carbonylation catalyst having a Group VIII metal selected from platinum or palladium or a compound containing the respective metal and tungsten associated with a solid carrier material. In a preferred embodiment, the catalyst includes a vaporous halide promoter component.

It is another object of the invention to provide a solid phase catalyst composition useful for vapor phase carbonylation of methanol to form acetic acid and/or methyl acetate.

These and other objects and advantages of the invention will become apparent to those skilled in the art from the accompanying detailed description.

DETAILED DESCRIPTION OF THE INVENTION

The solid supported catalyst of the present invention is particularly useful for the continuous production of carboxylic acids and esters by reacting lower alkyl alcohols, lower alkyl alcohol producing compositions such as ether derivatives of the alcohols and ester derivatives of the alcohols and mixtures therof in a vapor-phase carbonylation process. The solid supported catalyst includes an effective amount of a Group VIII metal selected from platinum or palladium and/or a compound containing the respective metal and tungsten and/or a tungsten containing compound wherein the metals are associated with a solid support material. Desirably, the solid support material is inert to the carbonylation reaction. In a particularly preferred embodiment, the catalyst further includes vaporous halide promoter component. The catalyst is particularly useful for producing acetic acid, methyl acetate and mixtures thereof from methanol and/or a methanol generating source using heterogeneous vapor-phase carbonylation. Desirably, the vapor-phase carbonylation process is operated at temperatures above the dew point of the reactant and product mixtures, i.e., the temperature at which condensation occurs. However, since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the reactants and product effluent. In practice, this generally dictates a temperature range of about 100° C. to about 500° C., with temperatures of about 100° C. to about 350° C. being preferred and temperatures of about 150° C. to 275° C. being particularly useful.

As with temperature, the useful pressure range is limited by the dew point of the product mixture. Provided that the reaction is operated at a temperature sufficient to prevent liquefaction of the reactants and products, a wide range of pressures may be used, e.g., pressures in the range of about 0.1 to 100 bars absolute (bara). The process preferably is carried out at a pressure in the range of about 1 to 50 bars absolute, most preferably, about 3 to 30 bar absolute.

Suitable feed stocks which may be carbonylated using the catalyst of the present invention include lower alkyl alcohols, lower alkyl alcohol producing compositions, such as ether and ester derivatives of the lower alkyl alcohol which generate a lower alkyl alcohol under vapor-phase carbonylation conditions, and mixtures thereof. Non-limiting examples of feed stocks include alcohols and ethers in which an aliphatic carbon atom is directly bonded to an oxygen atom of either an alcoholic hydroxyl group in the compound or an ether oxygen in the compound and may further include aromatic moieties. Preferably, the feed stock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxy-alkanols having from 3 to 10 carbon atoms. The most preferred reactant is methanol. Although methanol is the preferred feed stock to use with the solid supported catalyst of the present invention and is normally fed as methanol, it can be supplied in the form of a combination of materials which generate methanol. Examples of such materials include (i) methyl acetate and water and (ii) dimethyl ether and water. During carbonylation, both methyl acetate and dimethyl ether are formed within the reactor and, unless methyl acetate is the desired product, they are recycled with water to the reactor where they are converted to acetic acid.

The presence of water in the gaseous feed mixture is not essential when using methanol, the presence of some water is desirable to suppress formation of methyl acetate and/or dimethyl ether. When using methanol to produce acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When the catalyst is used in a vapor-phase carbonylation process to produce methyl acetate, no water should be added and dimethyl ether becomes the preferred feed stock. Further, when methanol is used as the feed stock in the preparation of methyl acetate, it is necessary to remove water. However, the primary utility of the catalyst of the present invention is in the manufacture of acetic acid.

The solid supported catalyst includes a catalytically effective amount of platinum or palladium associated with a solid support material. The compound or form of platinum or palladium used to prepare the solid supported catalyst generally is not critical and the catalyst may be prepared from any of a wide variety of platinum or palladium containing compounds. For example, platinum or palladium compounds may be alone or contain combinations of halide, trivalent nitrogen, organic compounds of trivalent phosphorous, carbon monoxide, hydrogen, and 2,4-pentanedione. Such materials are available commercially and may be used in the preparation of the catalysts utilized in the present invention. In addition, the oxides of platinum or palladium may be used if dissolved in the appropriate medium. Preferably the platinum or palladium is a salt of one of their respective chlorides. For example, based on the availability, cost and high solubility in water a preferred platinum or palladium is any of the various salts of hexachloroplatinate (IV) or a solution of platinum dichloride in either aqueous HCl or aqueous ammonia. Other suitable materials include platinum chloride or hexachloroplatinate complexes. One skilled in the art will understand that use of the preferred platinum or palladium complexes should be comparable on the basis of cost, solubility, and performance.

The amount of platinum or palladium, as metal, on the support can vary from about 0.01 weight percent to about 10 weight percent, with from about 0.1 weight percent to about 2 weight percent platinum or palladium being preferred based on the total weight of the solid supported catalyst.

The solid supported catalyst also includes a predetermined amount of tungsten as a second metal component. The form of tungsten used to prepare the catalyst generally is not critical. The solid phase component of the catalyst may be prepared from a wide variety of tungsten containing compounds. For example, tungsten compounds containing halides, a wide variety of organic (akyl and aryl) carboxylate salts, carbonyls, and alkyl or aryl groups bound to tungsten, as well as various mixtures thereof, are well known, are available commercially, and may be used in the preparation of the catalysts utilized in the present invention. In addition, there are a variety of tungsten oxides which may be used if dissolved in the appropriate medium. Based on its availability, cost, lower toxicity, and high solubility in water (the preferred solvent medium) the preferred source of tungsten is as the ammonium tungstate.

The content of tungsten, as metal, on the support can vary over a wide range, for example from about 0.01 to 10 weight percent tungsten based on the total weight of the solid supported catalyst. However, the preferred amount of tungsten in the catalyst is from about 0.1 to 5 weight percent of tungsten based on the total weight of the solid supported catalyst.

The solid support useful for acting as a carrier for the platinum or palladium and tungsten consists of a porous solid of such size that it can be employed in fixed or fluidized bed reactors. The support materials can have a size of from about 400 mesh per inch to about ½ inch. Preferably, the support is carbon, including activated carbon, having a surface area greater than about 200 square meters/gram ($m^2$/g). Activated carbon is well known in the art and may be derived from coal or peat having a density of from about 0.03 grams/cubic centimeter (g/$cm^3$) to about 2.25 g/$cm^3$. The carbon can have a surface area of from about 200 square meters/gram to about 1200 $m^2$/g. Other solid support materials may be used, either alone or in combination, in accordance with the present invention include pumice, alumina, silica, silica-alumina, magnesia, diatomaceous earth, bauxite, titania, zirconia, clays, magnesium silicate, silicon carbide, zeolites, and ceramics. The shape of the solid support is not particularly important and can be regular or irregular and include extrudates, rods, balls, broken pieces and the like disposed within the reactor.

The preparation of the solid support catalyst is carried out by preferably dissolving or dispersing the platinum or palladium and tungsten metal components in a suitable solvent. The solid support carrier material is then contacted with the metal containing solutions. Desirably, the Group VIII metal, i.e., platinum or palladium, and tungsten are associated with the support material as a result of soluble impregnation of the metals which may result in either a salt of the metals, an oxide of the metals, or as a free metal deposited on the support. Various methods of contacting the support material with the platinum or palladium and tungsten may be employed. For example, a solution containing the platinum or palladium can be admixed with a solution containing tungsten prior to impregnating the support material. Alternatively, the aforementioned individual solutions can be impregnated separately into or associated with the support material prior to impregnating the support material with the second metal containing solution. For example, the tungsten containing solution may be deposited on a previously prepared catalyst support having the platinum or palladium component already incorporated thereon. Desirably, in this alternative embodiment, the support is dried prior to contacting the second solution. Similarly, the platinum or palladium and tungsten may be associated with the support material in a variety of forms. For example, slurries of the metals can be poured over the support material, sprayed on the support material or the support material may be immersed in solutions containing excess platinum or palladium and tungsten with the excess being subsequently removed using techniques known to those skilled in the art. The solvent is evaporated so that at least a portion of the platinum or palladium and tungsten is associated with the solid support. Drying temperatures can range from about 100° C. to about 600° C. One skilled in the art will understand that the drying time is dependent upon the temperature, humidity, and solvent. Generally, lower temperatures require longer heating periods to effectively evaporate the solvent from the solid support.

The liquid used to deliver the platinum or palladium and tungsten in the form a solution, dispersion, or suspension is desirably a liquid having a low boiling point of from about 10° C. to about 140° C. Examples of suitable solvents include carbon tetrachloride, benzene, acetone, methanol, ethanol, isopropanol, isobutanol, pentane, hexane, cyclohexane, heptane, toluene, pyridine, diethylamine, acetaldehyde, acetic acid, tetrahydrofaran and preferably, water.

In a preferred embodiment, the catalyst system further includes a vaporous halide promoter selected from chlorine, bromine and iodine compounds. Preferably, the vaporous halide is selected from bromine and iodine compounds that are vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide, ethyl iodide, 1-iodopropane, 2-iodobutane, 1-iodobutane, methyl bromide, ethyl bromide, benzyl iodide and mixtures thereof. Desirably, the halide is a hydrogen halide or an alkyl halide having up to 6 carbon atoms. Non-limiting examples of preferred halides include hydrogen iodide, methyl iodide, hydrogen bromide, methyl bromide and mixtures thereof. The halide may also be a molecular halide such as $I_2$, $Br_2$, or $Cl_2$. Preferably, the halide is introduced into the carbonylation reactor with the reactants. As a result of contacting the active metal components with the halide promoter, the ultimate active species of the platinum or palladium and tungsten may exist as one or more coordination compounds or a halide thereof.

In practice, a gaseous mixture having at least one reactant of a lower alkyl alcohol, and/or a lower alkyl alcohol generating composition; carbon monoxide; and a halide are fed to a carbonylation reactor containing the solid supported platinum or palladium and tungsten catalyst described above. The reactant, in the vapor phase, is allowed to contact the solid supported catalyst. The reactor is maintained under vapor-phase carbonylation conditions of temperature and pressure. If acetic acid is the desired product, the feed stock may consist of methyl alcohol, dimethyl ether, methyl acetate, a methyl halide or any combination thereof. If it is desired to increase the proportion of acid produced, the ester may be recycled to the reactor together with water or introduced into a separate reactor with water to produce the acid in a separate zone. The process includes the steps of contacting a gaseous mixture comprising methanol, carbon monoxide and a vaporous halide promoter with the solid supported platinum or palladium and tungsten catalyst in a carbonylation zone and recovering a gaseous product from the carbonylation zone.

The molar ratio of methanol or methanol equivalents to halide present to produce an effective carbonylation ranges from about 1:1 to 10,000:1, with the preferred range being from about 5:1 to about 1000:1.

The carbon monoxide can be a purified carbon monoxide or include other gases. The carbon monoxide need not be of a high purity and may contain from about 1% by volume to about 99% by volume carbon monoxide, and preferably from about 70% by volume to about 99% by volume carbon monoxide. The remainder of the gas mixture including such gases as nitrogen, hydrogen, carbon dioxide, water and paraffinic hydrocarbons having from one to four carbon atoms. Although hydrogen is not part of the reaction stoichiometry, hydrogen may be useful in maintaining optimal catalyst activity. The preferred ratio of carbon monoxide to hydrogen generally ranges from about 99:1 to about 2:1, but ranges with even higher hydrogen levels are also likely to be useful.

The present invention is illustrated in greater detail by the specific examples present below. It is to be understood that these examples are illustrative embodiments and are not intended to be limiting of the invention, but rather are to be construed broadly within the scope and content of the appended claims.

In the examples which follow all of the catalysts were prepared in a similar manner except as specified otherwise.

EXAMPLES

Catalyst 1

In preparing the catalyst, 579 milligrams (mg) of dihydrogen hexachloroplatinate having a Pt assay of 39.23% (1.17 mmol of Pt) was dissolved in 30 milliliters (mL) of distilled water. This solution was then added to 20.0 grams of 12×40 mesh activated carbon granules (available from Calgon) contained in an evaporating dish. The activated carbon granules had a BET surface area in excess of 800 $m^2/g$. This mixture was dried using a steam bath and continuously stirred until the support granules became free flowing. The impregnated catalyst was then transferred to a quartz tube measuring 106 cm long by 25 mm outer diameter. The quartz tube was thereafter placed in a three-element electric tube furnace so that the mixture was located in the approximate center of the 61 cm long heated zone of the furnace. Nitrogen was continuously passed through the catalyst bed at a rate of 100 standard cubic centimeters per minute. The tube was heated from ambient temperature to 300° C. over a 2 hour period, held at 300° C. for 2 hours and then allowed to cool back to ambient temperature.

A second solution was prepared by dissolving 0.331 grams of ammonium tungstate (1.17 mm of W) in 30 mL of distilled water which had been heated to 50° C. to allow complete dissolution of the ammonium tungstate. This was then added to the Pt impregnated catalyst prepared above. The catalyst was dried and transferred to a quartz tube following the procedure described above.

The solid supported catalyst in accordance with the present invention (Catalyst 1) contained 1.09% Pt, 1.03% W, and had a density of 0.57 g /mL.

Catalyst Example 2

A second catalyst was prepared by dissolving 0.331 grams of ammonium tungstate (1.17 mmol) in 30 mL of distilled water which was heated to 50° C. to allow complete dissolution of the ammonium tungstate. This solution was then added to 20.0 grams of 12×40 mesh activated carbon granules (available from Calgon) contained in an evaporating dish. The activated carbon granules had a BET surface area in excess of 800 $m^2/g$. The mixture was then dried and placed in a quartz tube as described above in Example 1.

A second solution prepared by dissolving 0.207 grams of palladium chloride (1.1 6 mmol of Pd) in 15 mL of distilled water and 15 mL of 11.6 M HCl. This was then added to the tungsten impregnated catalyst prepared above. The mixture was again heated using the steam bath with continuous stirring until the granules became free flowing and then transferred to a quartz tube following the procedure described above.

Comparative Catalyst Example I

In preparing a comparative catalyst containing only platinum as the active metal, 569 mg of dihydrogen hexachloroplatinate having a Pt assay of 40% Pt (1.17 mmol of Pt) was dissolved in 30 milliliters (mL) of distilled water. This solution was added to 20.0 g of 12×40 mesh activated carbon granules contained in an evaporating dish. The activated carbon granules had a BET surface area in excess of 800 $m^2/g$. This mixture was heated using a steam bath and continuously stirred until the support granules became free flowing. The impregnated catalyst was then transferred to a quartz tube measuring 106 cm long by 25 mm outer diameter. The quartz tube was thereafter placed in a three-element electric tube furnace so that the mixture was located in the approximate center of the 61 cm long heated zone of the furnace. Nitrogen was continuously passed through the catalyst bed at a rate of 100 standard cubic centimeters per minute. The tube was heated from ambient temperature to 300° C. over a 2 hour period, held at 300° C. for 2 hours and then allowed to cool back to ambient temperature.

The catalyst (Comparative Catalyst C-I) contained 1.10% Pt and had a density of 0.57 g /mL.

Comparative Catalyst Example II

A second comparative catalyst (Comparative Catalyst C-II) was prepared following the procedure of Example 1 above except that 0.206 grams of ammonium molybdate (1.17 mmol) were used in place of ammonium tungstate. The ammonium molybdate dissolved at room temperature and did not require warming to 50° C.

Comparative Catalyst Example III

A third comparative catalyst (Comparative Catalyst C-III), was prepared following the procedure of Example 1 above except that 0.288 grams of chromium (III) acetate (1.117 mmol) were used in place of ammonium tungstate.

Comparative Catalyst Example IV

A fourth comparative catalyst (Comparative Catalyst C-IV), was prepared following the procedure of Comparative Catalyst Example 1 above except that 290 mg of nickelous acetate tetrahydrate (1.18 mmol of Ni) was used in place of the dihydrogen hexachloroplatinate. The catalyst contained 0.34% Ni.

Comparative Catalyst Example V

A fifth comparative catalyst (Comparative Catalyst C-V), was prepared by dissolving 0.331 grams of ammonium tungstate (1.17 mmol of W) in 30 mL of distilled water heated to 50° C. to allow complete dissolution of the ammonium tungstate. This solution was added to 20 grams of Davison Silica Grade 57, (available from W. R. Grace) contained in an evaporating dish. The silica had a BET surface area of 300 m$^2$/g. This mixture was dried using a steam bath and continuously stirred until the support granules became free flowing. The impregnated catalyst was then transferred to a quartz tube measuring 106 cm long by 25 mm outer diameter. The quartz tube was thereafter placed in a three-element electric tube furnace so that the mixture was located in the approximate center of the 61 cm long heated zone of the furnace. Nitrogen was continuously passed through the catalyst bed at a rate of 100 standard cubic centimeters per minute. The tube was heated from ambient temperature to 300° C. over a 2 hour period, held at 300° C. for 2 hours and then allowed to cool back to ambient temperature.

A second solution was prepared by dissolving 0.579 grams of dihydrogen hexachloroplatinate (IV) (1.16 mmol of Pt) in 30 mL of distilled water. This was then added to the tungsten impregnated catalyst above. The catalyst was dried and transferred to a quartz tube following the procedure described above.

Comparative Catalyst Example VI

A sixth comparative catalyst (Comparative Catalyst C-VI) was prepared following the procedure of Example 1 except that 20 g of α-alumina (Engelhard α-Alumina Al-3920T) having a BET surface area of 3–5 m$^2$/g was used in place of the activated carbon.

Comparative Catalyst Example VII

A seventh comparative catalyst (Comparative Catalyst C-VII) was prepared following the procedure of Example 2 except that 0.29 grams of nickelous acetate tetrahydrate dissolved in 30 mL of distilled water in place of the solution of palladium chloride in 1:1 concentrated HCl: water. The catalyst had a density of 0.57 g/ mL.

Comparative Catalyst Example VIII

An eighth comparative catalyst (Comparative Catalyst C-VIII) was prepared following the procedure of Comparative Example I above except 207 mg of palladium chloride (1.17 mmol of Pd) was used in place of the dihydrogen hexachloroplatinate and an additional 10 mL of concentrated HCl was added to solubilize the palladium chloride. This procedure gave a catalyst which contained. The catalyst contained 0.61% Pd and had a density of 0.57 g /mL.

Comparative Catalyst Example IX

A ninth comparative catalyst (Comparative Catalyst C-IX) was prepared following the procedure of Comparative Catalyst Example I above except 418 mg iridium trichloride hydrate (1.17 mmol of Ir) of was used in place of the dihydrogen hexachloroplatinate. The catalyst contained 1.10 weight % Ir.

Carbonylation of Menthol

The reactor system consisted of a 800 to 950 mm (31.5 and 37 inch) section of 6.35 mm (¼ inch) diameter tubing constructed of Hastelloy C alloy. The upper portion of the tube constituted the preheat and reaction (carbonylation) zones which were assembled by inserting a quartz wool pad 410 mm from the top of the reactor to act as support for the catalyst, followed sequentially by (1) a 0.7 gram bed of fine quartz chips (840 microns), (2) 0.5 gram of one of the catalysts prepared as described in the preceding examples, and (3) an additional 6 grams of fine quartz chips. The top of the tube was attached to an inlet manifold for introducing liquid and gaseous feeds.

The six grams of fine quartz chips acted as a heat exchange surface to vaporize the liquid feeds. Care was taken not to allow any liquid feeds to contact the catalyst bed at any time, including assembly, start-up, operation, and shutdown. The remaining lower length of tubing (product recovery section) consisted of a vortex cooler which varied in length depending on the original length of tubing employed and was maintained at approximately 0–5° C. during operation.

The gases were fed using Brooks flow controllers and liquids were fed using a high performance liquid chromatography pump. The gaseous products leaving the reaction zone were condensed using a vortex cooler operating at 0–5° C. The product reservoir was a tank placed downstream from the reactor system. The pressure was maintained using a Tescom 44-2300 Regulator on the outlet side of the reactor system and the temperature of the reaction section was maintained using heating tape on the outside of the reaction system.

Feeding of hydrogen and carbon monoxide to the reactor was commenced while maintaining the reactor at a temperature of 240° C. and a pressure of 17.2 bara (250 psia). The flow rate of hydrogen was set at 25 standard cubic cm. per minute (cc/min) and the carbon monoxide flow rate was set at 100 cc/min. The reactor section was maintained under these conditions for 1 hour or until the temperature and pressure had stabilized (whichever was longer.) The high pressure liquid chromatography pump was then started, feeding a mixture consisting of 70 weight percent methanol and 30 weight percent methyl iodide at a rate of 12 ml/min (The solution had a density of 1 g/mL.) Samples of the liquid product were collected and analyzed periodically using gas chromatographic techniques.

Carbonylation Example 1

The composition and weight of the samples taken periodically during the procedure described above in which Catalyst 1 was used are set forth in Table 1 wherein "Time" is the total time of operation (in hours) of the carbonylation commencing with the feeding of the methanol until a particular sample was taken. The values set forth below "MeI" (methyl iodide), "MeOAc" (methyl acetate), "MeOH" (methanol) and "HOAc" (acetic acid) are the weight percentages of each of those compounds present in the sample. The weight of each sample is given in grams.

TABLE I

| Sample Number | Expired Time (h) | MeI (Wt. %) | MeOAc (Wt. %) | MeOH (Wt. %) | HOAc (Wt. %) | Sample Weight (g) |
| --- | --- | --- | --- | --- | --- | --- |
| 1 | 3.5 | 16.11 | 35.79 | 19.73 | 15.46 | 46.2 |
| 2 | 5.5 | 15.99 | 36.48 | 19.89 | 15.37 | 29.8 |
| 3 | 8.5 | 16.15 | 36.43 | 19.72 | 15.27 | 30.9 |
| 4 | 10.5 | 17.97 | 31.22 | 30.24 | 6.82 | 29.6 |
| 5 | 15.5 | 17.8 | 31.34 | 30.27 | 6.8 | 75.6 |

TABLE I-continued

| Sample Number | Expired Time (h) | MeI (Wt. %) | MeOAc (Wt. %) | MeOH (Wt. %) | HOAc (Wt. %) | Sample Weight (g) |
|---|---|---|---|---|---|---|
| 6 | 18.0 | 15.85 | 36.19 | 19.59 | 15.19 | 32.9 |
| 7 | 23.5 | 15.87 | 35.76 | 19.57 | 15.31 | 70.2 |
| 8 | 26.5 | 17.11 | 33.42 | 25.75 | 9.83 | 29.9 |
| 9 | 30.5 | 16.63 | 33.22 | 25.73 | 9.93 | 60.9 |
| 10 | 35.0 | 16.86 | 31.09 | 30.59 | 8.06 | 41.5 |
| 11 | 39.5 | 18.09 | 31.13 | 29.55 | 8.45 | 80.1 |
| 12 | 41.5 | 18.13 | 31.15 | 29.48 | 8.34 | 28.5 |
| 13 | 47.5 | 18.09 | 31.14 | 29.5 | 8.39 | 76.5 |
| 14 | 49.5 | 18.5 | 31.82 | 30.35 | 8.62 | 26.2 |
| 15 | 51.5 | 18.72 | 31.48 | 29.89 | 8.42 | 23.9 |

The rate of acetyl production based on the preceding experiment utilizing Catalyst 1 is set forth in Table 2 below. The Sample Number and Time values correspond to those of Table 1. "Acetyl Produced" represents the quantity, in millimoles, of methyl acetate and acetic acid produced during each increment of Time. Acetyl Produced is calculated from the formula:

Acetyl Produced=(Sample weight (grams))×10×((weight % of MeOAc/74)+(weight % of AcOH/60)).

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour (space time yield) is determined as follows:

$$\frac{((\text{density of the catalyst (g/ml)}) \times (\text{Acetyl Produced}))}{((\text{grams of catalyst used}) \times (\text{Time Increment}))}$$

TABLE II

| Sample Number | Acetyl Produced (mmol) | Rate (mol/L-h) |
|---|---|---|
| 1 | 342.5 | 112 |
| 2 | 223.2 | 127 |
| 3 | 230.8 | 88 |
| 4 | 158.5 | 90 |
| 5 | 405.9 | 93 |
| 6 | 244.2 | 111 |
| 7 | 518.4 | 107 |
| 8 | 184.0 | 70 |
| 9 | 374.2 | 107 |
| 10 | 230.1 | 58 |
| 11 | 449.8 | 114 |
| 12 | 159.6 | 91 |
| 13 | 428.9 | 81 |
| 14 | 150.3 | 86 |
| 15 | 135.2 | 77 |

During the 51.1 hours of testing, the catalyst produced 4.24 moles of acetyl. This represents a rate of 165 moles of acetyl per kilogram of catalyst per hour (acetyl/kg$_{cat}$-h) or, represented as a space time yield, 94 mol of acetyl/L$_{cat}$-h.

Comparative Carbonylation Examples

Catalyst 2 Comparative Catalysts C-I through C-IX were used in the carbonylation of methanol using the same procedure and parameters as described above. The production Rate, expressed in terms of moles of Acetyl Produced per kilogram of catalyst per hour and moles per liter of catalyst volume per hour, for each of the catalysts is shown in Table 3 below.

TABLE III

| Carbonylation Example | Catalyst | Production Rate | |
|---|---|---|---|
| | | moles/kg$_{cat}$-h | moles/L$_{cat}$-h |
| 1 | 1 | 165 | 94 |
| C-1 | C-I | 89 | 45 |
| C-2 | C-II | 36 | 21 |
| C-3 | C-III | 21 | 12 |
| 2 | 2 | 77 | 44 |
| C-4 | C-IV | 3.0 | 1.7 |
| C-5 | C-V | 0.9 | — |
| C-6 | C-VI | 0 | 0 |
| C-7 | C-VII | 61 | 35 |
| C-8 | C-VIII | 1.7 | 0.8 |
| C-9 | C-IX | 93 | 53 |

As can be seen from Table III, the solid supported catalyst having platinum and tungsten on activated carbon is significantly more active than a catalyst derived from platinum alone. Moreover, it is surprising that promotional effect of tungsten is unique among the Group 6 (Cr, Mo, W) metals.

Carbonylation example 2, when compared to comparative example C-IV, demonstrates that there is a substantial promotion of palladium catalyzed reactions upon the addition of tungsten as well.

Moreover, as can be seen from carbonylation example C-9, the combination of platinum with tungsten is superior to comparative catalyst C-IX wherein iridium is the active metal. Surprisingly, the catalyst of the present invention exhibits commercially acceptable carbonylation rates in the substantial absence of other Group VIII compounds and particularly compounds containing rhodium, rhenium and iridium.

Although the present invention has been shown and described in terms of the presently preferred embodiment(s), it is to be understood that various modifications and substitutions, rearrangements of parts, components and process steps can be made by those skilled in the art without departing from the novel spirit and scope of the invention.

We claim:

1. A solid carbonylation catalyst useful for producing esters and carboxylic acids from reactants including lower alkyl alcohols and lower alkyl alcohol producing compositions in a vapor phase carbonylation process, said catalyst consisting essentially of a catalytically effective amount of a Group VIII metal selected from the group consisting of platinum, palladium, a platinum containing compound, and a palladium containing compound, and a Group VIB metal selected from the group consisting of tungsten and a tungsten containing compound and wherein said Group VIII and Group VIB metals are associated with a solid catalyst support material selected from carbon.

2. The solid carbonylation catalyst according to claim 1 wherein said solid support is activated carbon.

3. The solid carbonylation catalyst of claim 2 wherein said activated carbon has a BET surface area greater than about 800 m$^2$/gram.

4. The solid carbonylation catalyst of claim 1 wherein said catalyst includes from about 0.1 weight percent to about 10 weight percent each of said Group VIII metal and tungsten, wherein the weight percents of the metals is based on the total weight of the solid supported catalyst.

5. The solid carbonylation catalyst of claim 1 wherein said catalyst includes from about 0.1 weight percent to about 2 weight percent of said Group VIII metal and from about 0.1 to about 5 weight % of said tungsten, wherein the weight percents of the metals is based on the total weight of the solid supported catalyst.

6. The solid carbonylation catalyst of claim 1 wherein said Group VIII metal is platinum.

7. The solid carbonylation catalyst of claim 1 wherein said Group VIII metal is palladium.

8. The solid carbonylation catalyst of claim 1 further comprises a halogen promoting component selected from the group consisting of $I_2$, $Br_2$, and $Cl_2$, hydrogen halides, gaseous hydriodic acid, alkyl and aryl halides having up to 12 carbon atoms, and mixtures thereof.

9. The solid carbonylation catalyst of claim 8 wherein said halogen promoter is selected from the group consisting of hydrogen iodide, methyl iodide, ethyl iodide, 1-iodopropane, 2-iodobutane, 1-iodobutane, hydrogen bromide, methyl bromide, ethyl bromide, benzyl iodide and mixtures thereof.

10. The solid carbonylation catalyst of claim 1 wherein said Group VIII metal is selected from the group consisting of a salt of hexachloroplatinate (IV), platinum dichloride, platinum chloride and complexes of hexachloroplatinate.

11. The solid carbonylation catalyst of claim 10 wherein said Group VIII metal is selected from the group consisting of dihydrogen hexachloroplatinate and palladium chloride.

12. A solid carbonylation catalyst useful for producing acetic acid and methyl acetate from methanol and methanol generating compositions in a vapor phase carbonylation process, said catalyst consisting essentially of from about 0.1 weight percent to about 10 weight percent of a Group VIII metal selected from the group consisting of platinum and palladium, and from about 0.1 weight percent to about 10 weight percent of tungsten, wherein said metals are associated with a solid catalyst support material selected from activated carbon, and wherein the weight percents of the metals is based on the total weight of the solid supported catalyst.

13. The solid carbonylation catalyst of claim 12 wherein said catalyst includes from about 0.1 weight percent to about 2 weight percent of said Group VIII metal and from about 0.1 to about 5 weight % tungsten.

14. The solid carbonylation catalyst of claim 12 further comprising a halogen promoting component selected from the group consisting of hydrogen iodide, methyl iodide, ethyl iodide, 1-iodopropane, 2-iodobutane, 1-iodobutane, hydrogen bromide, methyl bromide, ethyl bromide, benzyl iodide and mixtures thereof.

15. The solid carbonylation catalyst of claim 14 wherein said activated carbon has a BET surface area greater than about 800 $m^2$/gram.

16. The solid carbonylation catalyst of claim 12 wherein said Group VIII metal is platinum.

17. The solid carbonylation catalyst of claim 12 wherein said Group VIII metal is palladium.

18. A solid carbonylation catalyst useful for producing acetic acid and methyl acetate from methanol and methanol generating compositions in a vapor phase carbonylation process, said catalyst consisting essentially of from about 0.1 weight percent to about 2 weight percent of Group VIII metal selected from the group consisting of platinum, palladium, a platinum containing compound, and a palladium containing compound, and from about 0.1 weight percent to about 5 weight percent of a Group VIB metal selected from the group consisting of tungsten and a tungsten containing compound, wherein said Group VIII and Group VIB metals are associated with activated carbon as a solid catalyst support material and wherein the weight percents of the metals is based on the total weight of the solid supported catalyst.

19. The solid carbonylation catalyst of claim 18 wherein said Group VIII metal is selected from the group consisting of a salt of hexachloroplatinate (IV), platinum dichloride, platinum chloride and complexes of hexachloroplatinate.

20. The solid carbonylation catalyst of claim 18 wherein said Group VIII metal is selected from the group consisting of dihydrogen hexachloroplatinate and palladium chloride.

21. The solid carbonylation catalyst of claim 18 further comprises a halogen promoting component selected from the group consisting of hydrogen iodide, methyl iodide, ethyl iodide, 1-iodopropane, 2-iodobutane, 1-iodobutane, hydrogen bromide, methyl bromide, ethyl bromide, benzyl iodide and mixtures thereof.

* * * * *